Aug. 10, 1971 G. K. Mc DANIEL Plant Pat. 3,059
ROSE PLANT
Filed April 14, 1969
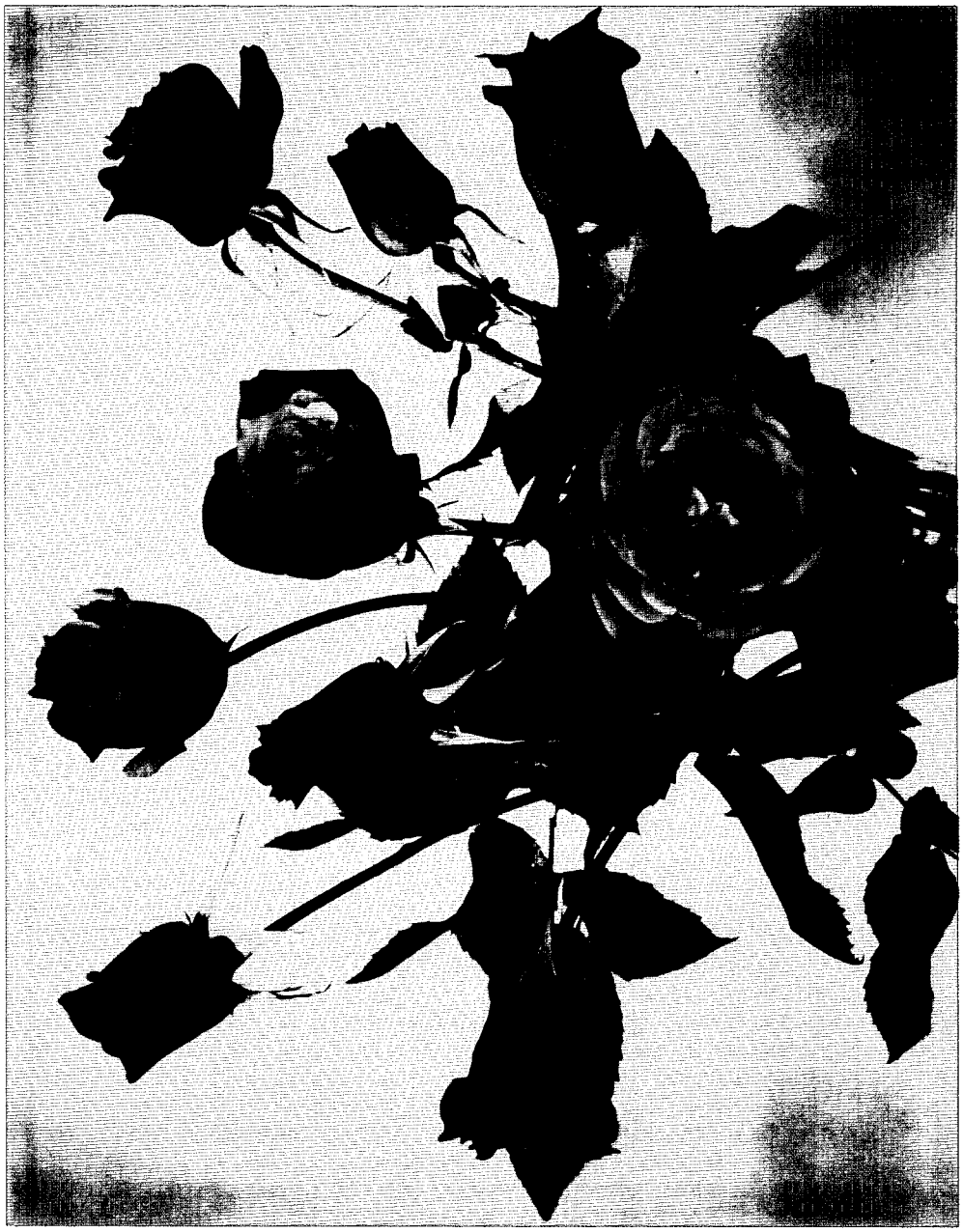
Inventor
Gayle Kent McDaniel

United States Patent Office

Plant Pat. 3,059
Patented Aug. 10, 1971

3,059
ROSE PLANT

Gayle Kent McDaniel, Carlton, Oreg., assignor to Carlton Rose Nurseries, Carlton, Oreg.

Filed Apr. 14, 1969, Ser. No. 816,130
Int. Cl. A01h *5/00*
U.S. Cl. Plt.—21 1 Claim

ABSTRACT OF THE DISCLOSURE

A hybrid tea rose plant of the greenhouse type, originated by crossing Happiness as the seed parent with an unknown red seedling.

The present invention relates to a new and distinct variety of rose plant of the hybrid tea class, particularly for greenhouse growing for cut flowers, which was originated by me by crossing the variety Happiness as the seed parent with an unknown red seedling.

The primary objective of this breeding was to produce a new rose variety especially which would grow tall in the greenhouse for cut flowers and would combine the vigor of bloom form and other desirable characteristics for this purpose.

Asexual reproduction of my new variety at Hillsboro, Oreg., shows that the characteristics come true to form and that the distinguishing characteristics hold through succeeding propagations by budding.

The accompanying drawing shows typical specimens of the growth and flower of my new variety in different stages of development and as depicted in color as nearly true as it is possible to make the same in color illustrations of this character.

The following is a detailed description of my new variety, with color terminology in accordance with the Dictionary of Color by A. Maerz and M. Rea Paul.

*Flower*

Flowers borne: Singly; regular; on normal, long stems,
Quantity of bloom: Free, in greenhouse.
Continuity: Continuous.
Fragrance: Moderate, sweetbriar.
Bud: Peduncle: short; medium; erect; green; entirely smooth; few hairs; green.
- *Before calyx breaks.*—Size: medium. Form: long pointed ovoid with a conspicuous neck without foliaceous appendages on the surface of the bud; with slender much-cut bristle-like foliaceous parts extending beyond the tip of the bud equal to ½ or more of its length.
- As the calyx breaks.—Color: Rubient Red, Plate 55, L 8.
- As first petal opens.—Size: medium. Form: Ovoid. Color: Outside: Hollyhock Red, Plate 53, L 11. Inside: Canyon Red, Plate 7, E 6.
- Opening.—It does open up well.

Bloom: Size when fully open: medium, 3¾ inches to 4¾ inches.
- *Petalage.*—Very double from 33 to 40 petals; arranged regularly.
- *Form.*—Full at first becoming flat; petals remaining at first flat outward; becoming later at maturity rolled outward.

Petals: thick; with inside velvety; outside satiny.
- Shape.—Outer: undulate, scalloped with base flat, with two notches. Intermediate: undulate, scalloped with apex flat; with one tooth. Inner: ovate; with apex flat.
- *Color.*—Colors may be modified by being washed with other colors.

This description of a newly opened flower was made from a rose grown in a greenhouse in January 1969, at Oregon Roses, Inc., Hillsboro, Oreg.
- *Color.*—Outer petal: Outside surface: Dark Peony Red, Plate 6, J–6. Inside surface: Garnet Red, Plate K–6. Intermediate petal: Outside surface: Light Peony Red, Plate 6, J–6. Inside surface: Gypsy Red, Plate 5, I–6. Inner petal: Outside surface: Strawberry, Plate 5, H–5. Inside surface Copper Rose, Plate 5, J–5.

This description was made from a rose that was open for three days in a greenhouse in January 1969, in Hayward, Calif.
- *Color.*—Outer petal: Outside surface: Ruby Red, Plate 6, G 6. Inside surface: Wild Cherry Red, Plate 6, C 6. Inner petal: Outside surface: Peony Red, Plate 6, J–6. Inside surface: Copper Rose, Plate 5, J–5.
- *General color effect.*—Newly opened flower: Luminous Afghan Red flower. Three days open: Sparkling Cerise flower.
- *Behavior.*—Persist; fading brown; affected by cold wet weather as follows: By producing smaller flowers.
- *Flower longevity.*—Cut roses grown in greenhouse in January, kept at living room temperatures nine days in January.

*Reproductive organs*

Stamens: Many; arranged regularly about pistils.
Filaments: Many; with anthers; medium long.
- *Color.*—Red-orange.

Anthers: All open at various times; large.
- *Color.*—Yellow with red mid rib. Seldom an anther fused with a petaloid.

Pollen: Moderate; yellow-gold.
Pistils: Many.
Styles: Uneven; medium long; heavy.
Stigma: Yellow.
Ovaries: Some protruding from receptacle.
Hips: Medium; pear shaped: smooth; walls fleshy; green.
Sepals: Permanent; long; spear shaped; recurved.
Seeds: Few; medium.

*Plant*

Foliage: Leaves: compound of three and five; sparse; medium-large; moderately soft.
- *Leaflets.*—Shape: ovoid, with apex acuminate, base round, margin serrate.
- *Color.*—Mature—Upper surface: Cossack Green, Plate 23, L 11. Under surface: Myto Green, Plate 20, B 5. Young—Upper surface: Cypress Green, Plate 23, L 6. Under surface: Surf Green, Plate 20, C 7.
- *Rachis (the supporting stem of the compound leaf).*—Medium. Upper side: smooth; grooved. Under side: extremely smooth.
- *Stipules.*—Very short; with long points turning out at an angle of less than 90°.
- *Disease.*—Resistant to mildew and blackspot.

Growth:
- *Habit*: Upright; branched.
- *Growth.*—Moderately vigorous.
- *Canes.*—Medium heavy.
- *Main stems.*—Bright. Color: Green French Green, Plate 29, D 8. Prickles: few, hooked downward. Color: Yellow Green. Hairs: none.
- *Branches.*—Bright. Color: Amazon Green, Plate 29, J 10. Prickles: several. Color: Dull red-green aging to Light Brown. Hairs: none. New Shoots: Bright. Color: Bronze Green Catawba, Plate 56, J 10.

Prickles: Several, hooked downward. Color: Bright Rosey Red base with transparent green tip. Hairs: None.

I claim:

1. A new and distinct variety of rose plant of the hybrid tea class substantially as herein shown and described, characterized particularly as to its hardy, tall growth for cut flowers, with the novelty of the blooms characterized by distinctive shades of red, the plant further being characterized by an upright growth, disease resistant.

No references cited.

ROBERT E. BAGWILL, Primary Examiner